United States Patent [19]
Bialsky et al.

[11] Patent Number: 5,157,961
[45] Date of Patent: Oct. 27, 1992

[54] APPARATUS FOR MEASURING THE RELATIVE AMOUNT OF A LIQUID IN A MIXTURE

[75] Inventors: Jacob Bialsky, Bnei Brak; Israel Levi, Haifa, both of Israel

[73] Assignee: Madid Industrial Controls Ltd., Haifa, Israel

[21] Appl. No.: 721,074

[22] Filed: Jun. 26, 1991

[30] Foreign Application Priority Data

Jul. 4, 1990 [IL] Israel .......................................... 94969

[51] Int. Cl.$^5$ .......................................... G01N 33/03
[52] U.S. Cl. ..................................... 73/53.01; 73/61.41
[58] Field of Search ................. 73/61.41, 61.43, 61.44, 73/53.01

[56] References Cited

U.S. PATENT DOCUMENTS

| | | | |
|---|---|---|---|
| 3,762,214 | 10/1973 | Bogusz | 73/61.41 |
| 3,861,198 | 1/1975 | Shea | 73/61.41 |
| 4,266,425 | 5/1981 | Allport | 73/61.41 |
| 4,359,638 | 11/1982 | Allport | 73/61.41 X |
| 4,679,426 | 7/1987 | Fuller et al. | 73/53.01 |
| 4,765,179 | 8/1988 | Fuller et al. | 73/53.01 |

*Primary Examiner*—Hezron E. Williams
*Assistant Examiner*—Joseph W. Roskos
*Attorney, Agent, or Firm*—Benjamin J. Barish

[57] ABSTRACT

Apparatus for measuring the relative amount of a liquid in a mixture of such liquid with another immiscible liquid and having radiation absorption characteristics differing therefrom includes a chamber for receiving the mixture, a high frequency antenna, an electrically-conductive shield, a cleaning device, and a drive for driving the cleaning device during the normal operation of the apparatus to prevent the accumulation of deposits which may affect the accuracy of the measurement or the need for frequently interrupting the use of the apparatus for cleaning purposes.

20 Claims, 2 Drawing Sheets

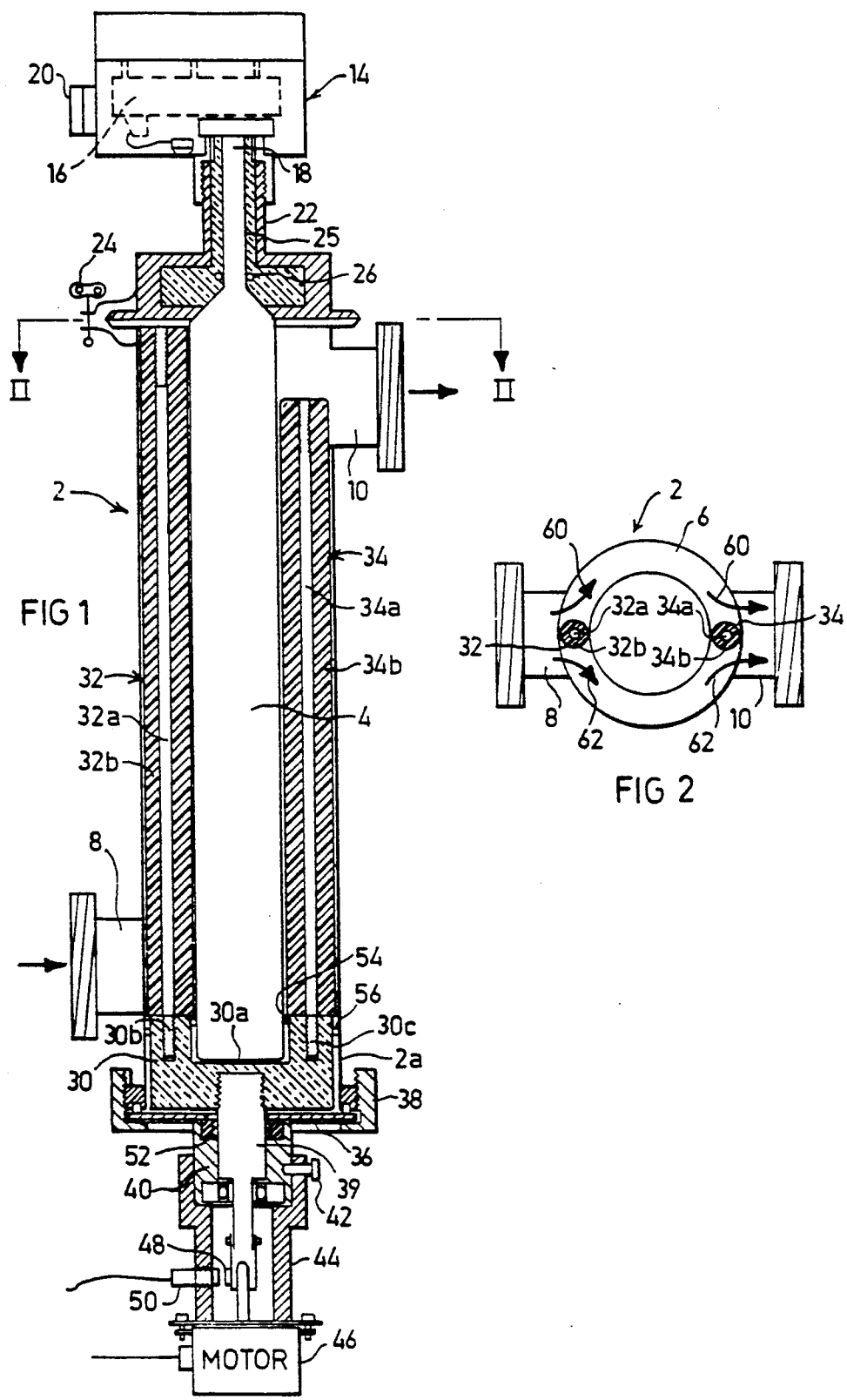

APPARATUS FOR MEASURING THE RELATIVE AMOUNT OF A LIQUID IN A MIXTURE

FIELD AND BACKGROUND OF THE INVENTION

The present invention relates to apparatus for measuring the relative amount of a liquid in a mixture including such a liquid with another liquid immiscible with respect thereto. An example of an application for such a measuring device is to measure the relative amount of water in margarine.

One known type of measuring device for measuring the relative amount of a liquid in a mixture is based on the measurement of the radiation absorption characteristics of such a mixture. Thus, when the two liquids have different known radiation absorption characteristics with respect to a high frequency antenna, measuring the radiation absorption characteristics of the mixture would provide a measurement of the relative amounts of the two liquids in the mixture. The known devices, however, are relatively inaccurate because of deposits from the mixture, and/or are frequently clogged by the mixture and therefore generally require a relatively large down-time for cleaning and maintainance purposes.

OBJECTS AND BRIEF SUMMARY OF THE INVENTION

An object of the present invention is to provide measuring apparatus of the foregoing type having advantages in the above respects.

According to the present invention, there is provided apparatus for measuring the relative amount of one liquid in a mixture including such liquid with another liquid immiscible with respect thereto and having radiation absorption characteristics differing therefrom, comprising: a high-frequency antenna for transmitting high-frequency radiation, and an electrically-conductive shield spaced from the antenna by a space including a surface receiving the mixture such that the radiation-absorption characteristics of the mixture may be measured to provide an indication of the relative amount of the one liquid in the mixture; characterized in that the apparatus further includes: a cleaning device in said space, and a drive for driving the cleaning device over the surface receiving the mixture to prevent the accumulation of deposits thereon.

Two embodiments of the invention are described below for purposes of example.

According to features in one described embodiment, the apparatus includes a housing having an annular feed chamber defining inner and outer annular surfaces contactible by the mixture, and means for receiving the antenna on one side of the feed chamber and the electrically-conductive shield on the other side of the feed chamber; the cleaning device being located in the feed chamber and being driven by the drive therethrough to prevent the accumulation of deposits on the inner and outer annular surfaces of the feed chamber.

According to features in the second described embodiment, the apparatus includes a conduit for conducting the mixture therethrough, and means for receiving the antenna and electrically-conductive shield on one side of the conduit; the electrically-conductive shield being coaxial with but spaced from the antenna by an end wall of insulating material closing the end of the antenna and electrically-conductive shield and disposed within the conduit such that the outer surface of the end wall is in contact with the mixture conducted through the conduit; the cleaning device being driven over the outer surface of the end wall to prevent the accumulation of deposits thereon.

Apparatus constructed in accordance with the foregoing features may be continuously cleaned during the normal operation of the apparatus, thereby preventing the accumulation of deposits which may affect the measurements or which may require relatively large down-time periods for cleaning and maintenance purposes.

Further features and advantages of the invention will be apparent from the description below.

BRIEF DESCRIPTION OF THE DRAWINGS

The invention is herein described, by way of example only, with reference to the accompanying drawings, wherein:

FIG. 1 is a longitudinal sectional view illustrating one form of measuring apparatus constructed in accordance with the present invention;

FIG. 2 is a transverse sectional view along line II—II of FIG. 1 but with the antenna removed;

DESCRIPTION OF PREFERRED EMBODIMENTS

Figure 3:
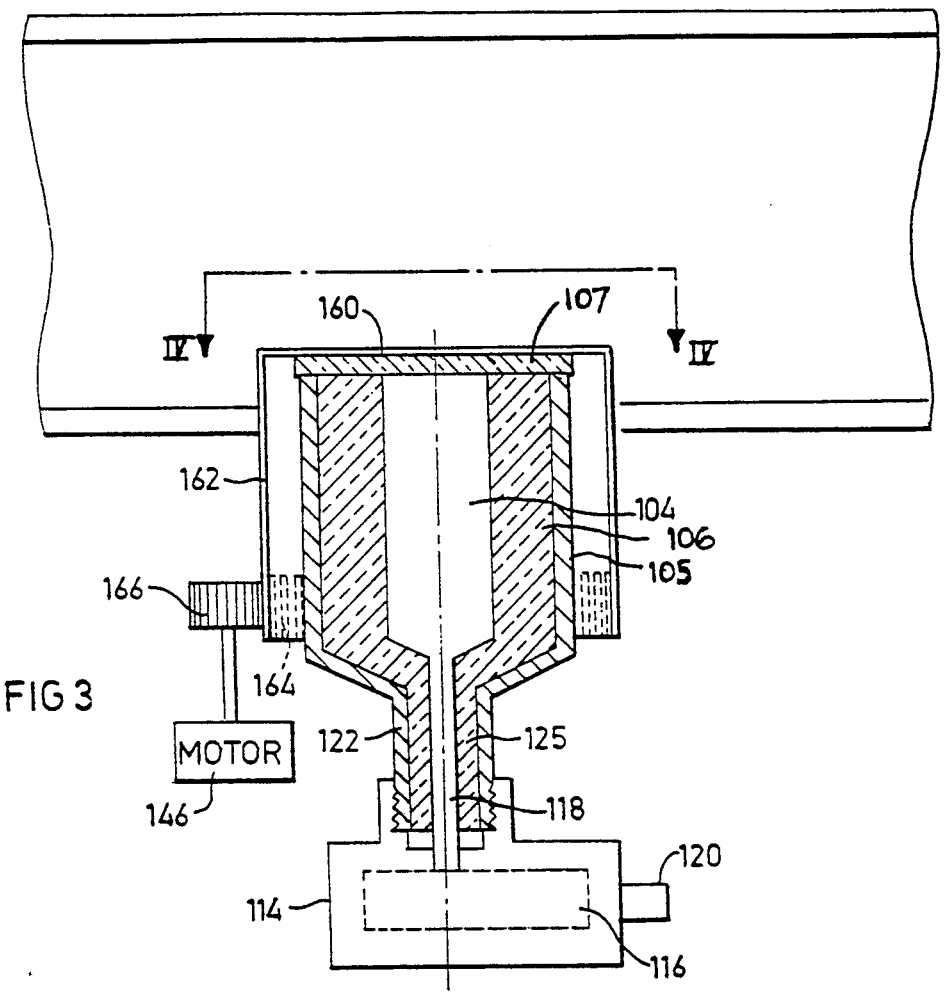
FIG. 3 is a longitudinal sectional view illustrating a second form of measuring apparatus constructed in accordance with the present invention.

The Embodiment of FIGS. 1 and 2

This embodiment is intended for measuring the relative amount of a liquid, such as water, in a mixture including such liquid with another liquid, such as margarine, or other liquid immiscible with respect to the first-mentioned liquid and having radiation absorption characteristics differing the from the first-mentioned liquid.

The measuring apparatus illustrated in FIGS. 1 and 2 comprises a housing, generally designated 2, of cylindrical configuration for receiving a cylindrical, high frequency antenna 4 of smaller diameter than the housing. Antenna 4 thus defines, with the inner surface of the housing 2, an annular feed chamber 6 for feeding the liquid through the housing from an inlet 8 to an outlet 10. Antenna 4 is provided with an outer insulated coating or layer so as to prevent direct contact between the metal of the antenna, and the feed mixture. Housing 2 is made of metal so that it itself serves as an electrically-conductive shield on the outer side of the feed chamber 6.

The high-frequency antenna 4 is carried by a second housing 14 of a high-frequency generator unit. Housing 14 further includes a high-frequency generator 16, a stub connector 18 for removably attaching antenna 4, and a cable inlet 20 for the electrical cables supplying power to the high-frequency generator 16. Housing 14 is also of metal and includes a metal extension 22 enclosing antenna 4 and connectible to the metal tube 2 by means of a mechanical connector 24 so as to complete the outer shield with respect to antenna 4. Housing 14 further includes insulating spacers 25 of suitable dielectric material, e.g., "Teflon" (Reg. T.M.), and a fluid seal 26 to prevent the feed mixture flowing through the outer annular chamber 4 from reaching the high-frequency housing 14.

The lower end of housing 2 includes an insulating holder 30 formed with a central socket 30a for receiving the antenna 4, and two sockets 30b, 30c, at diametrically-opposite points for receiving two cleaning rods 32, 34 extending axially through the annular feed chamber 6. Holder 30 is rotatable with respect to housing 2 so as to rotate the cleaning rods around the feed chamber 6. Each cleaning rod 32, 34 includes a metal core 32a, 34a, of smaller diameter than the width of the annular feed chamber 6, and a plastic sleeve 32b, 34b of a diameter substantially the same as the width of the annular feed chamber, so as to scrape the surfaces thereof when the rods are driven around the annular feed chamber. The plastic sleeves 32b, 34b may be, for example, a natural or synthetic elastomeric material. Thus, when the two cleaning rods 32, 34 are rotated around the annular feed chamber 6, they scrape away any particles clinging to the inner and outer annular surfaces of the feed chamber 6 in contact with the feed mixture and flush them out through the outlet 10.

As shown in FIG. 1, the two cleaning rods 32, 34 extend through the complete length of the annular feed chamber 6, from the holder 30 below the inlet 8 to the top of the chamber adjacent the outlet 10. Cleaning rod 32 is normally aligned with the axis of the inlet 8 and extends to the top of the housing 2, whereas cleaning rod 34 is normally aligned with the axis of the outlet 10 but ends slightly below the top of the housing.

As seen in FIG. 2, the diameters of the cleaning rods 32, 34 are substantially less than the diameters of the inlet 8 and outlet 10 so that, in the normal home position of the cleaning rods as shown in FIG. 2, they do not obstruct the flow of the liquid mixture from the inlet 8 to the annular feed chamber 6 and from the annular feed chamber 6 to the outlet 10.

Holder 30 is rotatably supported with respect to a fixed frame structure including a closure plate 36 fixed to housing 2 by means of a clamping ring 38. Holder 30 includes a drive shaft 39 passing through a bushing 40 and is secured at one end (e.g., by welding) to closure plate 36, and at the opposite end, e.g., by bolts 42, to a sleeve 44 enclosing the outer end of drive shaft 39. The latter end of the drive shaft is coupled to an electric motor 46. The outer end of drive shaft 39 further includes an actuator 48 cooperable with a limit switch 50 to automatically terminate the operation of the electric motor, and thereby the rotation of holder 30 and cleaning rods 32, 34, after the latter rods have been rotated one complete revolution from their normal position as illustrated in FIG. 2, back to their illustrated normal position.

A hydraulic seal 52 is provided in the passage of drive shaft 38 through closure plate 36. Further seals 54 and 56 are provided between the holder 30 and the antenna 4, and between the holder and the lower end of housing 2.

The measuring apparatus illustrated in FIGS. 1 and 2 of the drawings is operated as follows:

During the normal operation of the measuring apparatus, the feed mixture is fed via inlet 8 and flows through the annular feed chamber 6 to the outlet 10 while high-frequency radiation is transmitted by antenna 4 through the annular feed chamber to the outer wall of housing 2 which, being of metal and electrically grounded, serves as an electrically-conductive shield to the radiation. The absorption of the electrically-transmitted energy by the feed mixture in chamber 6 is measured to thereby provide an indication of the relative amount of one liquid (e.g., water) present in the mixture with the other liquid (e.g., margarine). Such measuring techniques are well-known in this type of equipment, and therefore are not described herein. As one example, the high-frequency generator 16 may generate energy at 3.8 MHz.

During this measuring mode of the apparatus, the two cleaning rods 32, 34 are located in their normal positions as illustrated in FIG. 2, aligned with the axes of the inlet 8 and outlet 10, respectively. Since the two cleaning rods 32, 34 are of smaller diameters than the inlet and outlet, they divide the flow of the liquid mixture into two streams, as shown by the arrows 60, 62 in FIG. 2, from the inlet 8 through the annular feed chamber 6 to the outlet 10.

Periodically or aperiodically, as desired, electric motor 46 is energized to rotate the cleaning rods 32, 34 through the annular feed chamber 6. During this cleaning mode, the plastic (e.g., elastomeric) sleeves 32b, 34b, carried by the cleaning rods 32, 34, engage the inner and outer annular surfaces of the feed chamber 6 and thus scrape away any particles tending to cling to them, which particles are flushed out through the outlet 10. Once electric motor 46 has been energized, it remains energized until holder 30 and the cleaning rods 32, 34 held by it complete a full rotation to return to their initial home positions aligned with the axes of the inlet 8 and outlet 10.

Thus, during the normal measuring mode of the apparatus, wherein the radiation absorption characteristics of the feed mixture are measured to thereby provide a measurement of the relative amounts of the liquids in the mixture, the cleaning rods 32, 34 do not obstruct the flow of the feed mixture through the annular feed chamber 6 since the two cleaning rods are of smaller diameter than the inlet 8 and outlet 10 and are aligned with their axes. Even in the cleaning mode, when the two cleaning rods 32, 34 are being rotated in the annular feed chamber 6, they also do not obstruct the flow of the feed mixture through the annular feed chamber since cleaning rod 34 terminates short of the top of the annular feed chamber 6, and therefore provides a bypass for the feed mixture flowing from the inlet 8 to the outlet 10. Accordingly, the illustrated apparatus may be operated continuously for measuring the relative amount of one liquid and feed mixture with respect to the other liquid with little or no down time for purposes of cleaning the annular feed chamber 6.

As one example, electric motor 46 may be energized to rotate the cleaning rods 32, 34, once every 5–15 minutes, according to the nature of the feed mixture, and may effect a complete revolution of the cleaning rods, terminated by the limit switch 50, during a time interval of 10–15 seconds.

Figure 4:
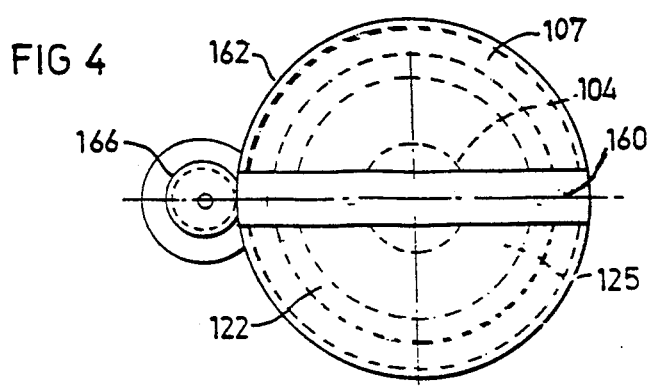
FIG. 4 is a top plan view of the apparatus of FIG. 3 along line IV–IV of FIG. 3.

The Embodiment of FIGS. 3 and 4

This embodiment may be used for the same purpose as that described above with respect to FIGS. 1 and 2, but here the mixture is conducted through a conduit 102 which receives the high-frequency generator unit 114 carrying the antenna 104, and the electrically-conductive shield 105 coaxial with the antenna and spaced therefrom by insulating material 106. In this case, the mixture, whose radiation-absorption characteristics are to be measured, contacts the outer surface of an insulating end wall 106 closing the end of the generator unit 114 and inserted within an opening in the conduit 102.

The generator unit 114 further includes a metal housing 115 enclosing a high-frequency generator 116, and a stub connector 118 connecting the generator to the antenna 104. The high-frequency generator 116 is fed by a cable inlet 120. The electrically-conductive shield 105 is formed with a reduced-diameter extension 122 threaded into metal housing 115 and insulated from the stub connector 118 by an insulating spacer 125.

The outer surface of end wall 107 is cleaned by a cleaning device which includes a cleaning member 160 applied diametrically across end wall 107 and carried at the end of a sleeve 162 enclosing the generator unmit 114. Sleeve 162 is spaced from the outer surface of the electrically-conductive shield 105 by a spacer-bearing 164, and is rotated by a drive wheel 166 rotated by drive motor 146.

Motor 146 may be operated, periodically or aperiodically as desired, in order to rotate sleeve 162, and thereby to rotate the cleaning member 160 over the outer surface of the end wall 107 in contact with the mixture flowing through the conduit 102. The operation of the cleaning device thus prevents the accumulation of deposits on the outer surface of end wall 107 without the need to interrupt the measuring operation or to down-time the apparatus for cleaning purposes.

While the invention has been described with respect to two preferred embodiments, it will be appreciated that many variations, modifications and other applications of the invention may be made.

What is claimed is:

1. Apparatus for measuring the relative amount of one liquid in a mixture including such liquid with another liquid immiscible with respect thereto and having radiation absorption characteristics differing therefrom, comprising: a high-frequency antenna for transmitting high-frequency radiation, and an electrically-conductive shield spaced from said antenna by a space including a surface receiving said mixture such that the radiation-absorption characteristics of the mixture may be measured to provide an indication of the relative amount of said one liquid in the mixture; characterized in that said apparatus further includes: a cleaning device in said space, and a drive for driving said cleaning device over said surface receiving said mixture to prevent the accumulation of deposits thereon.

2. The apparatus according to claim 1, wherein said apparatus further includes a housing having an annular feed chamber defining inner and outer annular surfaces contactible by the mixture, and means for receiving said antenna on one side of the feed chamber and said electrically-conductive shield on the other side of said feed chamber; said cleaning device being located in said feed chamber and being driven by said drive therethrough to prevent the accumulation of deposits on said inner and outer annular surfaces of the feed chamber.

3. The apparatus according to claim 2, wherein said means for receiving the high frequency antenna is located centrally of said housing to receive the antenna axially of the housing, said electrically-conductive shield being outwardly of said feed chamber.

4. The apparatus according to claim 3, wherein said cleaning device comprises at least one cleaning rod extending axially of and movable around said feed chamber.

5. The apparatus according to claim 4, wherein said cleaning rod includes a metal core of smaller diameter than the width of said annular feed chamber, and a plastic sleeve of substantially the same diameter as the width of said annular feed chamber so as to scrape the sides thereof when the rod is driven around said annular feed chamber.

6. The apparatus according to claim 3, wherein said cleaning device comprises at least two cleaning rods in parallel spaced relation to each other extending axially of and movable around said annular feed chamber.

7. The apparatus according to claim 6, wherein said cleaning rods are normally located in alignment with, and are of smaller diameter than, the inlet and outlet of the feed chamber so as not to interfere with the flow of the feed mixture through said feed chamber during the normal operation of the device.

8. The apparatus according to claim 7, wherein one of said rods is of shorter length than the other of said rods to provide a bypass for the feed mixture flowing from said inlet to said outlet during a cleaning operation of the feed chamber by said cleaning rods.

9. The apparatus according to claim 7, wherein said means for receiving said antenna comprises a rotatable holder formed with sockets for receiving one end of said antenna and said rods.

10. The apparatus according to claim 9, wherein said rotatable holder is at one end of the housing, said antenna being receivable through an opening in the opposite end of the housing.

11. The apparatus according to claim 1, wherein the apparatus further includes a conduit for conducting the mixture therethrough, and means for receiving said antenna and electrically-conductive shield on one side of the conduit; said electrically-conductive shield being coaxial with but spaced from the antenna by an end wall of insulating material closing the end of the antenna and electrically-conductive shield and disposed within the conduit such that the outer surface of said end wall is in contact with the mixture conducted through the conduit; said cleaning device being driven over said outer surface of the end wall to prevent the accumulation of deposits thereon.

12. The apparatus according to claim 11, wherein said cleaning device includes a cleaning member extending diametrically across the outer surface of said end wall, and a sleeve enclosing said antenna and said electrically-conductive shield and carrying said cleaning member; said drive being coupled to said sleeve to rotate it and the cleaning member carried thereby.

13. The apparatus according to claim 12, wherein said electrically-conductive shield is located between said antenna and said sleeve of the cleaning device.

14. Apparatus for measuring the relative amount of a first liquid in a mixture including said liquid with another liquid immiscible with respect thereto and having radiation absorption characteristics differing therefrom, comprising:
   a housing including an annular feed chamber for feeding the mixture therethrough from an inlet through an outlet;
   a high frequency unit including a generator and an antenna projecting from one end of the unit and received in said housing on one side of said feed chamber;
   an electrically-conductive shield on the opposite side of said feed chamber;
   a cleaning device in said feed chamber for cleaning same;
   and a drive for driving said cleaning device around said annular feed chamber.

15. The apparatus according to claim 14, wherein said cleaning device comprises at least one cleaning rod extending axially of and movable around said annular feed chamber.

16. The apparatus according to claim 15, wherein said cleaning rod includes a metal core of smaller diameter than the width of said annular feed chamber, and a plastic sleeve of substantially the same diameter as the width of said annular feed chamber so as to scrape the sides thereof when the rod is driven around said annular feed chamber.

17. The measuring device according to claim 16, wherein said cleaning device comprises at least two of said cleaning rods in parallel spaced relation to each other extending axially of and movable around said annular feed chamber.

18. The apparatus according to claim 17, wherein said cleaning rods are normally located in alignment with, and are of smaller diameter than, the inlet and outlet of the feed chamber so as not to interfere with the flow of the feed mixture through said feed chamber during the normal operation of the device.

19. Apparatus for measuring the relative amount of a first liquid in a mixture including said liquid with another liquid immiscible with respect thereto and having radiation absorption characteristics differing therefrom, comprising:

a conduit for conducting the mixture therethrough;

a high frequency unit including a generator, an antenna, an electrically-conductive shield coaxial with but spaced from the antenna, and an end wall of insulating material closing the end of the antenna and shield and adapted to be disposed on one side of the conduit such that its outer surface is in contact with the mixture conducted therethrough;

a cleaning device in contact with the outer surface of said end wall;

and a drive for rotating said cleaning device over said outer surface of the end wall to prevent the accumulation of deposits thereon.

20. The apparatus according to claim 19, wherein said cleaning device includes a cleaning member extending diametrically across the outer surface of said end wall, and a sleeve enclosing said antenna and said electrically-conductive shield and carrying said cleaning member; said drive being coupled to said sleeve to rotate it and the cleaning member carried thereby.

* * * * *